US006354136B1

(12) United States Patent
Bremer et al.

(10) Patent No.: US 6,354,136 B1
(45) Date of Patent: Mar. 12, 2002

(54) GAS CHROMATOGRAPH WITH A TEMPERATURE-CONTROLLED INJECTOR

(75) Inventors: Ralf Bremer, Oberhausen; Bernhard Rose, Dusseldorf, both of (DE)

(73) Assignee: Gerstal GmbH Co., KG (DE)

( * ) Notice: Subject to any disclaimer, the term of this patent is extended or adjusted under 35 U.S.C. 154(b) by 0 days.

(21) Appl. No.: 09/264,797

(22) Filed: Mar. 9, 1999

(30) Foreign Application Priority Data

Mar. 10, 1998 (DE) .......................................... 198 10 109

(51) Int. Cl.[7] .......................... G01N 33/00; G01N 30/04; B01D 15/08; B09B 3/00
(52) U.S. Cl. .......................... 73/23.35; 73/23.41; 95/89; 95/87; 210/198.2; 96/105; 422/89
(58) Field of Search ........................... 73/23.35, 23.41, 73/61.55, 61.57, 51.56, 19.02; 210/198.2; 62/55.5, 600, 617, 904; 95/87, 89; 96/104.105; 422/89

(56) References Cited

U.S. PATENT DOCUMENTS

| 3,366,149 | A | * | 1/1968 | Taft et al. ....................... 141/82 |
| 3,735,565 | A | * | 5/1973 | Gilby et al. ................... 55/197 |
| 3,996,009 | A | * | 12/1976 | Fine et al. ................. 23/254 R |
| 4,024,752 | A | * | 5/1977 | Orlando ....................... 73/17 A |
| 4,045,998 | A | * | 9/1977 | Ford ............................ 73/23.1 |
| 4,526,686 | A | * | 7/1985 | Sisti et al. ................ 210/198.2 |
| 5,152,176 | A | * | 10/1992 | Bryselbout et al. ......... 73/23.41 |
| 5,390,529 | A | * | 2/1995 | Ghiselli ...................... 73/23.41 |
| 5,394,733 | A | * | 3/1995 | Acholla ....................... 73/23.41 |
| 5,402,668 | A | * | 4/1995 | Murakami et al. .......... 73/19.02 |
| 5,547,497 | A | * | 8/1996 | Klemp et al. ................... 96/104 |
| 5,596,876 | A | | 1/1997 | Manura et al. ............... 62/55.5 |
| 5,665,314 | A | * | 9/1997 | Berger et al. .................. 422/89 |
| 5,672,810 | A | * | 9/1997 | Shibamoto ................. 73/23.25 |
| 5,922,106 | A | * | 7/1999 | Mowry et al. .................. 95/87 |

* cited by examiner

Primary Examiner—Hezron Williams
Assistant Examiner—David J. Wiggins
(74) Attorney, Agent, or Firm—Patterson, Thuente, Skaar & Christensen, P.A.

(57) ABSTRACT

The invention relates to a gas chromatograph having a temperature-controlled injector for containing a vaporizer tube with chemical substances, thereon to be analyzed via a gas chromatography column, which temperature-controlled injector and vaporization tube can be heated by an electric resistance coil type of heating unit and can be cooled by a cooling unit, wherein the cooling unit has a cooling coil (7) which surrounds the heating unit and which is provided via a feedline and a return line (8, 9) with an external source of liquid, cooled coolant, with provision of a pump (11) for circulating the coolant and of a drain valve for draining the cooling coil.

8 Claims, 2 Drawing Sheets

GAS CHROMATOGRAPH WITH A TEMPERATURE-CONTROLLED INJECTOR

BACKGROUND OF THE INVENTION

The invention relates to a gas chromatograph having a temperature-controlled injector.

Gas chromatographs may have different types of injectors for material to be investigated by gas chromatography, for example cold injection units, thermodesorption units, split units, traps (cryotraps), which require cooling in certain phases of operation in order, for example, to bring about adsorption of material to be investigated and/or prevent desorption thereof.

For example, German Patent 34 48 091 C3 discloses a cold injection unit in which an injection needle is used to deliver material to be investigated into a vaporizer tube which is connected via a transfer line to a capillary chromatography column. The vaporizer tube is surrounded by a heating unit in the form of a coiled resistance heater which is arranged inside a covering leaving a gap. On the outside of the covering there is provided a Peltier thermoelectric element for cooling. Apart from the fact that only a relatively small Peltier element with correspondingly low power can ordinarily be used for reasons of space, also the heat transmission to the vaporizer tube is poor, the temperature profile is uneven, and the reaction time is too long.

The alternate possibility of employing cryocooling would, apart from the disadvantages associated therewith in relation to the storage of coolant, lead to nitrogen or carbon dioxide, which are used in this case, getting from the gap between the coiled heating unit and covering into the oven chamber, which contains the capillary column, of a gas chromatograph and adversely affecting the programmed temperature and desired temperature profile prevailing therein.

SUMMARY OF THE INVENTION

It is an object of the preferred embodiments of the invention to provide a gas chromatograph provided with a cooling unit which makes it possible to cool a temperature-controlled injector with a rapid reaction time and a required temperature profile.

An example of a preferred embodiment of the invention concerns a gas chromatograph, comprising:
- a temperature-controlled injector provided with a heating unit for heating the injector and a cooling unit concentrically surrounding the heating unit for cooling the injector;
  - wherein the cooling unit has a cooling coil which surrounds the heating unit and which cooling unit is provided via a feed line and a return line with an external source of liquid, cooled coolant, and
  - wherein a pump for circulating the coolant and a drain valve for draining the cooling coil are provided.
  Further objects, advantages and embodiments of the invention are evident from the following description.

The invention is explained in more detail hereinafter by means of an exemplary embodiment of the invention shown in the attached drawings.

DETAILED DESCRIPTION

Figure 1:
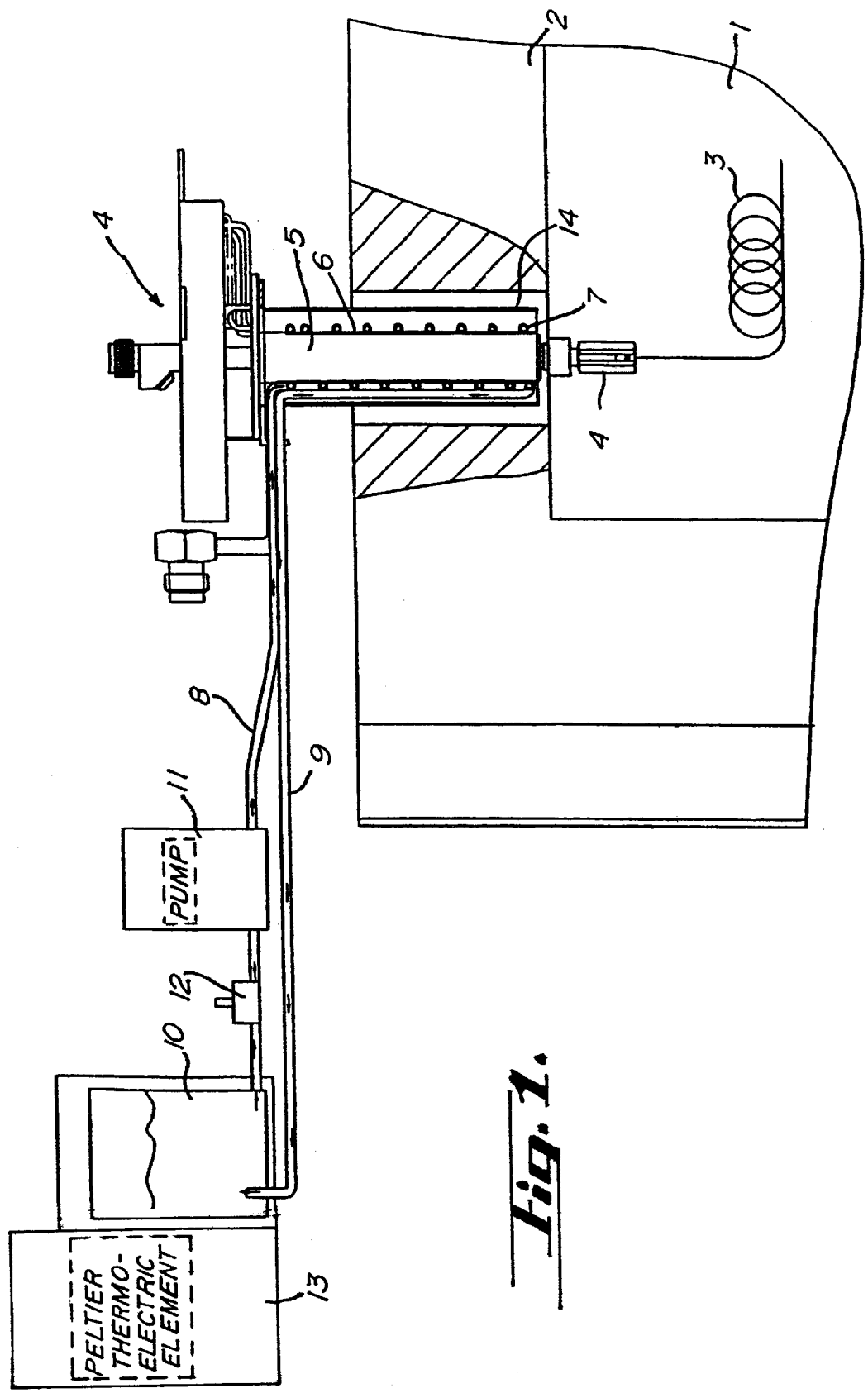
FIG. 1 shows diagrammatically and in section a gas chromatograph according to the invention.

The gas chromatograph shown in FIG. 1 comprises a heatable oven 1 with a thermally insulated wall 2 in which a capillary column 3 is arranged, to which substances to be analyzed are fed for example using a carrier gas via a cold injection unit 4.

The cold injection unit 4 comprises a receiver for a vaporizer tube which is surrounded by the heating coils of a resistance heating unit and can be heated by the heating unit with a predetermined temperature profile in order, for example, for substances adsorbed on a liner in the vaporizer tube to be vaporized and fed to the capillary column 3 via an adapter 4' by means of a carrier gas such as nitrogen for the purpose of investigation by gas chromatography. For injection of a sample, an injection needle is inserted sealingly as far as the vaporizer tube, and then the sample is injected into the cold vaporizer tube, which is then heated for split or splitless injection of the sample into the capillary column 3. An expedient embodiment of the heating device as shown at position 5 in FIG. 1, which preferably has a metallic protective tube 5, is described in the German Patent 195 20 715 C1.

The cold injection unit 4 is inserted into a metallic jacket 6, preferably providing a metallic contact between the jacket 6 and the protective tube 5 or the outside of the heating unit (shown at position 5), in order to bring about heat transmission through metallic heat induction.

A cooling coil 7 is located on the jacket 6 and is connected via a feed line 8 and a return line 9 to an external reservoir 10, which is arranged remote from the oven 1, for liquid coolant, in particular water. The internal diameter of the cooling coil 7 and of the feed line and return line 8, 9 is generally in the range from about 0.8 to 1.2 mm. The liquid volume in the coolant circulation is generally in the range from about 20 to 40 ml. In the feed line 8 there is a pump 11 for circulating the coolant and a drain valve 12, for example a 3/2-way valve, for draining the cooling coil 7 and admitting air.

The reservoir 10 is expediently cooled by means of a Peltier thermoelectric element 13 which can be designed to be sufficiently large to provide a large cooling capacity, which makes a rapid reaction time possible. In this case, no safety monitoring in relation to the coolant is necessary either, because no external coolant reserves are required.

However, instead of this it is also possible to use a cryostat, in which case the cooling coil 7 forms the vaporizer thereof, which is connected via the feed line and return line 8, 9 to the condenser (as at position 10) which is cooled, for example, by a fan (as at position 13).

If no special cooling capacity is required, the reservoir 10 can also be cooled by cold water from a water line.

Also provided where appropriate is an additional connector which opens into the region between the cooling coil 7 and an outer jacket 14, for cooling by means of liquid nitrogen or carbon dioxide.

Since the coolant circulation is a liquid circulation, it is necessary to drain the coolant out of the cooling coil before the heating process via the pump 11 and the drain of all 12, so that at least part of the heat produced during the heating is not used to vaporize the liquid coolant, which would result in a temperature plateau on heating (undesirable occurrence), whereas a rapid and steady heating is desirable.

Figure 2:
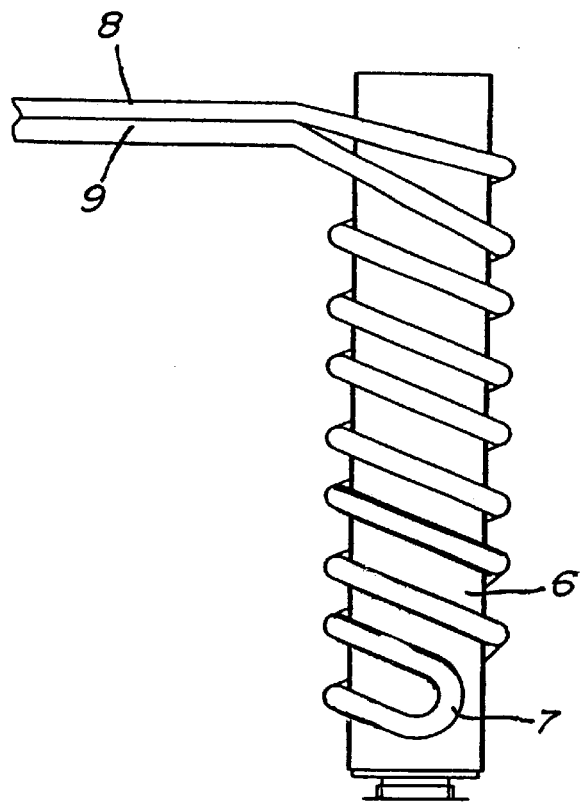
FIGS. 2 and 3 show in developed view two embodiments of cooling coils for the gas chromatograph of FIG. 1.
Figure 3:
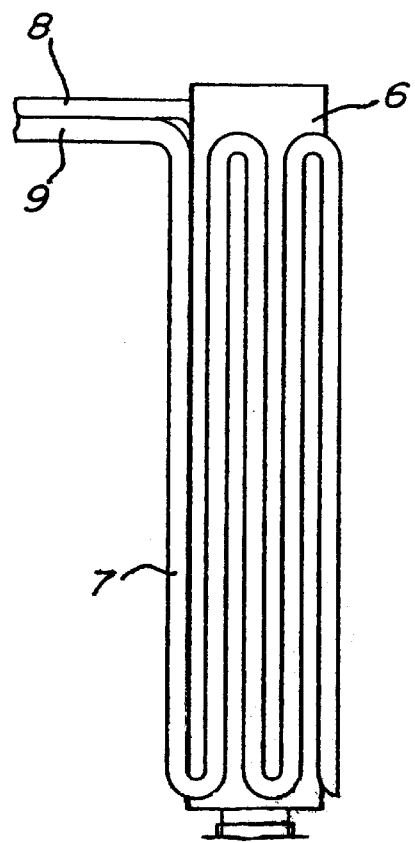

The cooling coil 7 can be wound, in particular, in such a way that both its entry and its exit end are located on one side of the cooling coil 7. Meandering or bifilar winding of the cooling coil 7 is possible for this purpose, cf. FIGS. 2 and 3. It is also possible to attain fine tuning of the cold thermal injection process by appropriate variation in the winding, for the cooling capacity to be varied over the length of the jacket 6, for example to be enhanced at the end facing the oven 1.

Although the foregoing has been a description of the preferred embodiment of the invention, it will be apparent to those skilled in the art that numerous variations and modifications may be made to the invention without departing from the scope as described herein.

What is claimed is:

1. A temperature-controlled injector for a gas chromatograph, the injector provided with a heating unit for heating the injector and a cooling unit concentrically surrounding the heating unit for cooling the injector;

wherein the cooling unit has a cooling coil which surrounds the heating unit and which is provided via a feed line and a return line with an external source of liquid, cooled coolant, and wherein the cooling coil is arranged on a jacket into which the injector with the heating unit is insertable and;

wherein a pump for circulating the coolant and a drain valve for draining the cooling coil are provided.

2. The injector of claim 1, wherein the source is a reservoir provided with a Peltier element for cooling the reservoir.

3. The injector of claim 1, wherein the source is a condenser of a cryostat provided with a vaporizer which forms the cooling coil.

4. The injector of claim 1, wherein the cooling coil has meandering or bifilar winding with an entry end and an exit end, the entry and exit ends thereof being located next to one another on one.

5. A gas chromatograph, comprising:

a temperature controlled injector;

a heating unit for heating the injector;

a cooling unit for cooling the injector, said cooling unit comprising a cooling coil surrounding the heating unit, said cooling coil provided with an external source of liquid, cooled coolant via a feed line and a return line;

a pump for circulating the coolant; and a drain valve for draining the cooling coil.

6. The gas chromatograph of claim 5, wherein the source is a reservoir provided with a Peltier element for cooling the reservoir.

7. The gas chromatograph of claim 5, wherein the source is a condenser of a cryostat provided with a vaporizer which forms the cooling coil.

8. The gas chromatograph of claim 5, wherein the cooling coil has meandering or bifilar winding with an entry end and a exit end, the entry and exit ends thereof being located next to one another on one end of the cooling coil.

* * * * *

UNITED STATES PATENT AND TRADEMARK OFFICE
CERTIFICATE OF CORRECTION

PATENT NO.    : 6,354,136 B1
DATED         : March 12, 2002
INVENTOR(S)   : Rolf Bremer and Bernhard Rose It is certified that error appears in the above-identified patent and that said Letters Patent is hereby corrected as shown below:

<u>Title page,</u>
Item [73], Assignee, please delete "Gerstal GmbH & Co., KG" and insert in its place -- Gerstel GmbH & Co., KG --.

<u>Column 4,</u>
Line 7, please insert after "surrounding the heating unit" -- and arranged on a jacket, the injector and the heating unit insertable in the jacket --.

Signed and Sealed this

Third Day of September, 2002

Attest:

Attesting Officer

JAMES E. ROGAN
*Director of the United States Patent and Trademark Office*